United States Patent [19]

Karrer et al.

[11] 4,017,549
[45] * Apr. 12, 1977

[54] DIPHENYLMETHANE ETHER DERIVATIVES

[75] Inventors: Friedrich Karrer, Basel; Saleem Farooq, Aesch, both of Switzerland

[73] Assignee: Ciba-Geigy Corporation, Ardsley, N.Y.

[*] Notice: The portion of the term of this patent subsequent to May 18, 1993, has been disclaimed.

[22] Filed: Oct. 20, 1975

[21] Appl. No.: 623,876

[30] Foreign Application Priority Data

Oct. 24, 1974 Switzerland .................. 14246/74
Sept. 23, 1975 Switzerland .................. 12337/75

[52] U.S. Cl. .................. 260/613 R; 260/609 F; 424/341
[51] Int. Cl.² .................. C07C 43/20
[58] Field of Search .................. 260/613 R

[56] References Cited
UNITED STATES PATENTS

| | | | |
|---|---|---|---|
| 3,131,166 | 4/1964 | Harris et al. | 260/613 R X |
| 3,340,308 | 9/1967 | Sterling et al. | 260/613 R |
| 3,600,437 | 8/1971 | Marshall | 260/613 R X |

Primary Examiner—Bernard Helfin
Attorney, Agent, or Firm—Harry Falber

[57] ABSTRACT

New diphenylmethane and diphenylthioether derivatives of the formula

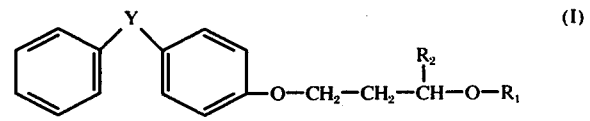

(I)

wherein
  $R_1$ represents a $C_3$–$C_5$-alkenyl, $C_3$–$C_5$-chloroalkenyl or $C_3$–$C_5$-alkynyl radical,
  $R_2$ represents a hydrogen atom or a methyl radical, and
  Y represents a sulphur atom or a methylene group, which are effective against pests, processes for their production, as well as compositions and methods for the control of pests by use of the new derivatives as active substances are described.

5 Claims, No Drawings

DIPHENYLMETHANE ETHER DERIVATIVES

The present invention relates to new 4-substituted diphenylmethane derivtives and diphenylthioether derivatives which are effective against pests, to processes for the production of these derivatives, as well as to compositions and processes for the control of pests by use of the new derivatives as active substances.

The new compounds according to the invention correspond to the formula I

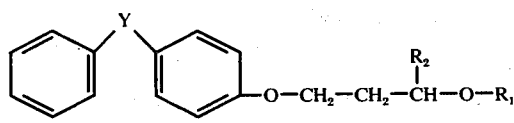  (I)

wherein
$R_1$ represents a $C_3$–$C_5$-alkenyl, $C_3$–$C_5$-chloroalkenyl or $C_3$–$C_5$-alkynyl radical,
$R_2$ represents a hydrogen atom or a methyl radical, and
Y represents a sulphur atom or a methylene group.

Alkenyl, chloroalkenyl and alkynyl radicals denoted by $R_1$ can be branched-chain or straight-chain. Alkenyl and chloroalkenyl radicals are, e.g., the allyl or 2-butenyl radical such as the 1-methylallyl, 2-methylallyl, 3-methylallyl or 1,2-dimethylallyl radical, as well as their chlorine-substituted derivatives such as the 1-chloroallyl, 2-chloroallyl, 2-chloromethylallyl and 1-methyl-2-chloroallyl radical. Suitable alkynyl radicals to be mentioned are, inter alia, the propargyl, but-3-in-2-yl and 2-methyl-but-3-in-2-yl radical.

Compounds of the above-mentioned formula I which are of particular importance on account of their action on pests, particularly on insects, especially on larvae and pupae of insects, and on member of the order Acarina, are those wherein
$R_1$ represents an allyl, 2-butenyl, 3-chloroallyl or propargyl radical.

As examples there may be mentioned compounds of the formula I for which $R_1$, $R_2$ and Y have the following meanings:

| $R_1$ | $R_2$ | Y |
|---|---|---|
| CH≡C—CH$_2$— | CH$_3$— | —CH$_2$— |
| CH$_2$=CH—CH$_2$— | CH$_3$— | —CH$_2$— |
| Cl—CH=CH—CH$_2$— | CH$_3$— | —CH$_2$— |
| CH$_2$=CH—CH$_2$— | H | —CH$_2$— |
| Cl—CH=CH—CH$_2$— | H | —CH$_2$— |
| CH≡C—CH(CH$_3$)— | CH$_3$— | —CH$_2$— |
| CH≡C—CH$_2$— | H | —CH$_2$— |
| CH≡C—CH(CH$_3$)— | H | —CH$_2$— |
| CH≡C—CH$_2$— | CH$_3$— | S |
| CH≡C—CH(CH$_3$)— | CH$_3$— | S |
| Cl—CH=CH—CH$_2$— | CH$_3$— | S |
| CH$_3$—CH=CH—CH$_2$— | CH$_3$— | S |
| CH≡C—CH$_2$— | H | S |
| CH≡C—CH(CH$_3$)— | H | S |
| Cl—CH=CH—CH$_2$— | H | S |
| CH$_3$—CH=CH—CH$_2$— | H | S |

The new compounds of the formula I are advantageously obtained by methods known per se; for example, by a process wherein
a. a compound of the formula II

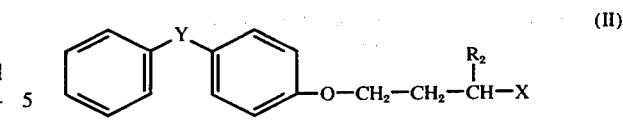  (II)

is reacted with a compound of the formula III

MOR$_1$  (III);

b. a compound of the formula IV

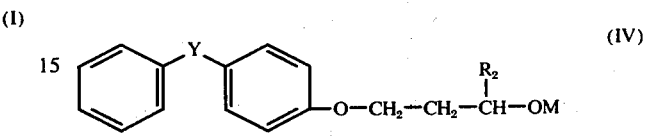  (IV)

is reacted with a compound of the formula V

X—R$_1$  (V);

or
c. a compound of the formula VI

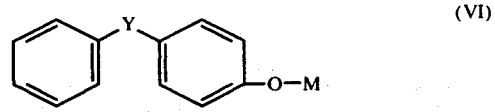  (VI)

is treated with a compound of the formula VII

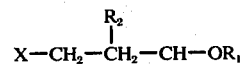  (VII);

X—CH$_2$—CH$_2$—CH—OR$_1$ in which formulae II to VII
M stands for a metal ion of the main group I or II of the periodic system, particularly for a sodium, potassium or lithium ion,
X represents a halogen atom, especially a chlorine or bromine atom, and
$R_1$ and $R_2$ have the meanings given under formula I.

Depending on the reactivity of the applied halide of the formulae II, V and VII, these processes can be performed in various solvents and at different reaction temperatures, preferably in the presence of at least one mole of a base.

Suitable solvents are, in particular, 1,2-dimethoxyethane, tetrahydrofuran, dioxane, dialkyl ether, dimethylformamide, dimethylsulphoxide, hexamethylphosphoric acid triamide and sulpholane. It is however possible to use other solvents. Examples of suitable bases are alkali metal hydroxides, alkali metal carbonates and alkali metal hydrides, as well as alkali metal alkoxides. The reaction temperatures for processes (a) and (b) are between 0° and 100° C, mostly between 10° and 80° C, and for process (c) between room temperature and 120° C, usually between 20° and 100° C.

The reactions in certain cases can advantageously be carried out in a protective gas atmosphere, e.g. in a nitrogen atmosphere.

The starting materials of the formulae III and V to VII are known from the literature, while those of the formulae II and IV are easily obtainable from known intermediates, e.g. by a. reaction of a compound of the above mentioned formula VI in the presence of a solvent, such as acetone, with a halide of the formula VIII $$X-CH_2-CH=CH-R_2 \quad (VIII)$$

wherein X represents a halogen atom, preferably a chlorine or bromine atom; reaction of the resulting reaction product of the formula IX

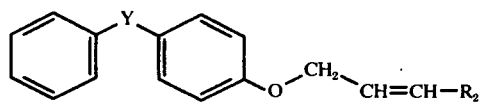

with water in the presence of a mercury(II)-salt, especially mercury(II)-acetate or mercury(II)-trifluoroacetate, to give a compound of the formula (X)

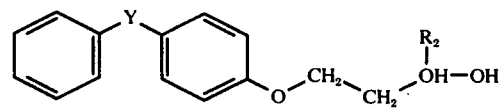

and subsequent treatment of this compound, for example with an alkali metal hydride, in the presence of tetrahydrofuran and/or hexamethylphosphoric acid triamide, as a result of which there is formed a compound of the formula IV above, wherein M represents an alkali metal ion; or b. reaction of a compound of the previously given formula VI with a dihalide of the formula XI

wherein X represents a halogen atom, preferably a chlorine or bromine atom, to obtain a compound of the formula II wherein $R_2$ stands for a hydrogen atom.

Compounds of the formula I wherein $R_2$ represents a methyl radical can be present in different optically active isomers. If therefore in such cases in the production process no optically active starting materials are used, then there are necessarily obtained racemic mixtures. Also cis/trans isomeric mixtures are obtainable if $R_1$ denotes a substituted alkenyl radical, e.g. a halogenoallyl radical.

The various mixtures of isomers can be separated into the cis/trans isomers, e.g., by means of chromatographical separation methods, e.g. by adsorption on a separating material having selective adsorption activity, such as silica gel or aluminium oxide, and subsequent elution of the separated isomers with a suitable solvent, e.g. diethyl ether, hexane, methyl acetate or ethyl acetate, etc.. A further chromatographical separation method is gas chromatography. In certain cases, a cis/trans isomeric mixture can be separated also by fractional distillation or by fractional crystallisation.

It is understood that the present invention embraces both specific sterioisomers or cis/trans isomers and the mixtures thereof.

The active substances of the formula I are suitable for the control of pests, particularly for the control of phytopathogenic insects, especially of eggs, larvae and pupae of insects, and members of the order Acarina; and particularly for the control of pests in fruit growing, for example in the case of citrus fruit, and of pests affecting hygiene.

Examples of families of insects and Acarina against which the active substances of the formula I have a positive effect are:

Insects:

Acrididae, Blattidae, Gryllidae, Gryllotalpidae, Tettigoniidae, Cimicidae, Pyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae;

Acarina:

Ixodidae, Argasidae, Tetranychidae and Dermanyssidae.

Other biological active substances or compositions may be added to the described compositions of the invention. For the widening of their range of action, the new compositions can contain, in addition to the stated compounds of the general formula I, for example: insecticides, fungicides, bactericides, fungistatics, bacteriostatics or nematocides.

A further factor to be emphasised is the low toxicity of the compounds of formula I to warm-blooded animals.

The compounds of formula I can be used on their own or together with suitable carriers and/or additives. Suitable carriers and additives may be solid or liquid, and they correspond to the substances common in formulation practice, such as natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The compositions according to the invention are produced in a manner known per se by the intimate mixing and/or grinding of active substances of formula I with suitable carriers, optionally with the addition of dispersing agents or solvents that are inert to the active substances. The active substances can be obtained and used in the following forms:

solid preparations:

dusts, scattering agents or granulates (coated granultes, impregnated granulates and homogeneous granulates);

liquid preparations:

a. water-dispersible active-substance concentrates: wettable powders, pastes or emulsions, b. solutions: aerosols.

The active substances of formula I can be formulated, for example, as follows (parts denote parts by weight):

Dusts:

The following substances are used to produce (a) a 5%, dust, and (b) a 2% dust:

a.

5 parts of active substance, 95 parts of talcum;

b.

2 parts of active substance, 1 part of highly dispersed silicic acid, 97 parts of talcum.

The active substances are mixed and ground with the carriers.

Granulate:

The following substances are used to produce a 5% granulate:

5 parts of active substance,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The solution thus obtained is sprayed on to kaolin, and the acetone is subsequently evaporated off in vacuo.

Wettable powder:

The following constituents are used in the preparation of (a) a 40% (b) and (c) a 25%, and (d) a 10% wettable powder:

a.
40 parts of active substance,
5 parts of sodium lignin sulphonate,
1 part of sodium dibutyl-naphthalene sulphonate,
54 parts of silicic acid;

b.
25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid
19.5 parts of Champagne chalk,
28.1 parts of kaolin;

c.
25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminum silicate,
16.5 parts of kieselguhr,
46 parts of kaolin;

d.
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives; the mixture is then ground in the appropriate mills and rollers. Wettable powders are obtained which can be diluted with water to give suspensions of any desired concentration.

Emulsifiable concentrates:

The following substances are used to produce (a) a 10%, (b) a 25% and (c) a 50% emulsifiable concentrate:

a.
10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

b.
25 parts of active substance,
2.5 parts of epoxidised vegetable oil,
10 parts of alkylarylsulphonate/fatty alcoholpolyglycol ether mixture,
5 parts of dimethylformamide,
57.5 parts of xylene;

c.
50 parts of active substance,
4.2 parts of tributylphenol-polyglycol ether,
5.8 parts of calcium-dodecylbenzenesulphonate,
20 parts of cyclohexanone,
20 parts of xylene.

It is possible to prepare from these concentrates, by dilution with water, emulsions of any desired concentration.

Spray:

The following constituents are used to produce (a) a 5% spray and (b) a 95% spray:

a.
5 parts of active substance,
1 part of epichlorohydrin,
94 parts of ligroin (boiling limits 160–190° C);

b.
95 parts of active substance,
5 parts of epichlorohydrin.

The following Examples serve to further illustrate the invention.

EXAMPLE 1

Production of 1-(4-benzyl)-phenoxy-3-propargyloxy-propane of the formula:

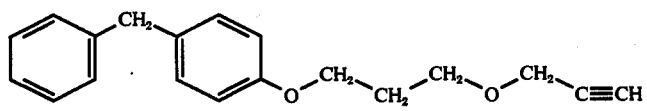

7.2 g of sodium hydride dispersion in mineral oil (containing about 60% of NaH) was washed successively with hexane and tetrahydrofuran; it was then covered with 120 ml of pure tetrahydrofuran and 80 ml of dimethylformamide. To this suspension, under an $N_2$ protective-gas atmosphere, there was added dropwise at room temperature in the course of about 15 minutes, with stirring, 14 g of propargyl alcohol in 10 ml of tetrahydrofuran, and the mixture was heated with stirring for a further 3 hours at 30°–35° C. There was then added dropwise to the reaction mixture at room temperature, within 30 minutes, the solution of 45.8 g of 1-(4-benzyl)-phenoxy-3-bromopropane [$n_D^{20}$: 1.5820: produced from 4-benzylphenol and 1,3-dibromopropane by a process analogous to that used by C. S. Marvel et al. (J. Amer. Chem. Soc. 44, 2647 (1922)) for 3-bromo-1-phenoxypropane] in 50 ml of dimethylformamide, and stirring was maintained for a further 8 hours at room temperature and 4 hours at 60°–65° C. In subsequent processing, ice-water was carefully added to the reaction mixture, and extraction was repeatedly performed with hexane and ether. The combined organic phases were then washed several times with water and saturated sodium chloride solution, dried over sodium sulphate and freed in vacuo from the solvents. The oily-like crude product was further purified by chromatography on silica gel (eluant: diethyl-ether/hexane 1:6) to obtain pure 1-(4-benzyl)-phenoxy-3-propargyloxy-propane (Compound No. 1) having a refractive index of $n_D^{20}$: 1.5574.

EXAMPLE 2

There were produced by a process analogous to that of Example 1 the following compounds of the formula I in which the symbols $R_1$, $R_2$ and Y have the meanings given below in the table (cis/trans isomeric mixtures indicated by asterisks):

| Comp. No. | $R_1$ | $R_2$ | Y | Physical data $n_D^{20}$ |
|---|---|---|---|---|
| 2 | $CH_2=CH-CH_2-$ | H | $-CH_2-$ | 1,5487 |
| 3 | $CH_2=CH-CH_2-$ | $CH_3-$ | $-CH_2-$ | 1,5495 |
| 4* | $Cl-CH=CH_2-CH_2-$ | H | $-CH_2-$ | 1,5590 |
| 5* | $Cl-CH=CH-CH_2-$ | H | S | 1,6104 |
| 6* | $CH_3-CH=CH-CH_2-$ | H | S | 1,5810 |
| 7 | $CH\equiv C-CH_2-$ | H | S | 1,5879 |

EXAMPLE 3

A. Contact action on Dysdercus-fasciatus larvae

A specific amount of a 0.1% acetonic active-substance solution (corresponding to 10 mg of active substance per square meter) was transferred by pipet to an aluminium dish and uniformly distributed. After evaporation of the acetone, 10 larvae in the fifth stage of Dysdercus fasciatus were placed into the treated dish containing feed and moist cotton wool. The dish was then covered with a perforated lid. After about 10 days, i.e. as soon as the control insects had moulted into adults, the test insects were examined to determine the number of normal adults.

The compounds 1-7 exhibited a good action in the above test.

B. Contact action on *Aedes-aegypti larvae*

About 20 two-day-old larvae of the yellow-fever mosquito (Aedes aegypti) were placed in position in a beaker containing a solution of the active substance (concentration 5 ppm). The beaker was then covered with a perforated lid. After the control insects had moulted into adults, the test insects were examined and the percentage of normal adults in comparison with the control adults was determined.

The compounds 1-7 exhibited a good action in the above test.

C. Contact action on Tenebrio-molitor pupae

A specific amount of a 0.1% acetonic active-substance solution corresponding to 10 mg of active substance per square meter was transferred by pipet into an aluminum dish and uniformly distributed. After evaporation of the acetone, 10 freshly formed pupae were placed onto the treated surface, and the dish was covered with a perforated lid. After the control insects had left the cocoon as imagines, the test insects were examined to determine the number of normal adults.

The compounds -1-exhibited a good action in the above test.

D. Action on eggs of Spodoptera littoralis

Eggs of *Spodoptera littoralis* were immersed in, or wetted with, an acetonic or acetonic-aqueous solution containing 0.05% of active substance. It was subsequently determined whether or not larvae would develop from the treated eggs.

The compounds 1-7 severely inhibited the development of larvae.

EXAMPLE 4

A. Action on Musca domestica

An amount in each case of 50 g of CSMA maggot substrate was weighed off in beakers. For each active substance, 2.5 ml of a 1% acetonic solution of the respective substance was transferred by pipet twice to 50 g of maggot substrate each time. After a thorough mixing of the treated substrate, the solvent was allowed to evaporate. There were then deposited per active substance in each case 25 one-, two- and three-day-old maggots and about 50 fly eggs. After completion of pupation, the pupae were flushed out and counted. After a period of ten days, the number of emerged flies was counted and hence any effect on metamorphosis was established.

The compounds 1-7 exhibited in this test a good effect against *Musca domestica*.

B. Action on Ephestia Kuhniella 50 g of wheat flour was made up in two beakers with a specific amount of active substance to give a 5% dust, the concentration of active substance being 0.05%. Into each beaker (25 g of flour) there were placed 10 larvae of *Ephesta Kuhniella*. The pattern of population was ascertained after a period of 8 weeks and the number of moths was determined.

The compounds 1-7 exhibited in this test a good effect against *Ephestia Kuhniella*.

We claim:

1. A compound of the formula I

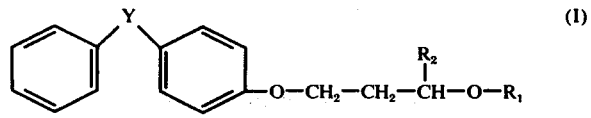

wherein
$R_1$ represents a $C_3-C_5$-alkenyl, $C_3-C_5$-chloroalkenyl or $C_3-C_5$-alkynyl radical,
$R_2$ represents a hydrogen atom or a methyl radical, and
Y represents a methylene group.

2. The compound according to claim 1 wherein $R_1$ represents an allyl, 2-butenyl, 3-chloroallyl or propargyl radical.

3. 1-(4-Benzyl)-phenoxy-3-propargyloxy-propane according to claim 1.

4. 1-(Benzyl)-phenoxy-3-(3-chloroallyloxy)-propane according to claim 1.

5. 1-(4-Benzyl)-phenoxy-3-allyloxy-propane according to claim 1.

* * * * *